(12) United States Patent
Ling et al.

(10) Patent No.: US 6,960,475 B2
(45) Date of Patent: Nov. 1, 2005

(54) COMPOSITION AND PROCESS FOR INDICATING THE PRESENCE OF SOLUBLE FLUORIDE ION IN ORAL CARE COMPOSITIONS AND METHOD OF MAKING THE SAME

(75) Inventors: Junjian Ling, Beijing (CN); Hai Ye, Beijing (CN); Christopher David Buckley, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 492 days.

(21) Appl. No.: 10/188,613

(22) Filed: Jul. 3, 2002

(65) Prior Publication Data

US 2003/0031633 A1 Feb. 13, 2003

Related U.S. Application Data

(60) Provisional application No. 60/304,669, filed on Jul. 11, 2001.

(51) Int. Cl.⁷ ............................ A61K 7/18; G01N 33/00
(52) U.S. Cl. ......................................... 436/124; 424/52
(58) Field of Search ........................................... 436/124

(56) References Cited

U.S. PATENT DOCUMENTS

| 1,006,908 | A |   | 10/1911 | Palin |         |
|-----------|---|---|---------|-------|---------|
| 1,007,024 | A |   | 10/1911 | Earnheart | |
| 3,202,616 | A | * | 8/1965  | Johnson | 436/125 |
| 3,458,286 | A |   | 7/1969  | Pallin |         |
| 5,053,339 | A | * | 10/1991 | Patel | 436/2 |
| 6,375,934 | B1 | * | 4/2002 | Eklund et al. | 424/52 |

FOREIGN PATENT DOCUMENTS

JP     61 2819 63     6/1985

* cited by examiner

*Primary Examiner*—Monique T. Cole
(74) *Attorney, Agent, or Firm*—Betty J. Zea

(57) ABSTRACT

Disclosed is a process for indicating the presence of soluble fluoride ions in oral care compositions comprising making a signal solution and then bringing the signal solution into contact with an oral care composition and a color change occurs if an effective amount of soluble fluoride ion is present in the oral care composition. Further disclosed are test compositions for use in such process.

10 Claims, No Drawings

COMPOSITION AND PROCESS FOR INDICATING THE PRESENCE OF SOLUBLE FLUORIDE ION IN ORAL CARE COMPOSITIONS AND METHOD OF MAKING THE SAME

CROSS REFERENCE TO RELATED APPLICATION

This application claims the benefit of U.S. Provisional Application No. 60/304,669 filed Jul. 11, 2001.

FIELD OF THE INVENTION

The present invention relates to a composition and a process for indicating the presence of soluble fluoride ions in an oral care composition. Specifically, the present invention relates to the use of color indicator in combination with a metal ion to form a composition that interacts with soluble fluoride ions causing a color change to indicate when an effective amount of soluble fluoride ion is present in an oral care composition.

BACKGROUND OF THE INVENTION

Good oral hygiene may be at least in part achieved by brushing the teeth with an oral care composition such as a dentifrice composition. A dentifrice composition is widely acknowledged as important in contributing to improving oral health, especially via a reduction in the incidence of dental caries and the build-up of tartar and dental calculus. Such conditions result from oral plaque, and may lead to diseases such as periodontis and gingivitis. These diseases remain a major cause of tooth loss in adults today. In addition, other oral health afflictions, such as staining of the tooth enamel and oral malodor (bad breath) may be reduced by regular tooth brushing with a dentifrice composition.

Fluoride ion sources are well known for use in oral care compositions as anti-caries agents. Soluble fluoride ions are contained in a number of oral care compositions for this purpose, particularly toothpaste. Application of soluble fluoride ions to dental enamel serves to protect teeth against decay. A wide variety of fluoride ion-yielding materials can be employed as sources of soluble fluoride in oral care compositions.

While some oral care compositions may contain fluoride ions, the source of such fluoride ions may not be effective to provide sufficient anti-caries benefits. For example, certain fluoride sources react with free ions from abrasives in the oral care composition to form insoluble salts such as calcium fluoride ($CaF_2$). This kind of fluoride is not soluble and therefore is ineffective against preventing caries. However, the average consumer has no way of knowing whether the fluoride ion source in his or her oral care composition is delivering an effective amount of soluble fluoride ion. Therefore, it would be beneficial to have a fluoride detecting means that is easy to use for consumers.

Like oral care compositions, water sources sometimes contain fluoride. Various processes and products are available for testing the concentration of fluoride in water. There are several known chemical reactions that test for the presence and concentration of soluble fluoride ions in water. Exemplary of some of the various forms of these chemical reactions is GB 1,006,908.

However these chemical processes are designed for large-scale industrial use, such as wastewater treatment, and are expensive on a smaller scale. These processes and products often involve several steps that require precision and often take place at acidity levels unacceptable for consumer use. Additionally, the processes for testing water often involve lengthy periods of time for results to occur. Reaction rates requiring more than 15 minutes are not ideal for a consumer product.

Accordingly, the need exists for a fast, cost effective, easy and accurate system for indicating the presence of effective soluble fluoride ion sources in oral care compositions that is easy for consumers to use at home and/or for oral care professionals to use in the office.

SUMMARY OF THE INVENTION

The present invention is directed to a process for indicating the presence of soluble fluoride ions in oral care compositions comprising making a signal solution and then bringing the signal solution into contact with an oral care composition; wherein a color change occurs if an effective amount of soluble fluoride ion is present in the oral care composition.

The present invention is further directed to a test composition comprised of aluminon, aluminum ion, and buffer that can be used to indicate the presence of soluble fluoride ions in oral care compositions.

These and other features, aspects, advantages, and variations of the present invention, and the embodiments described herein, will become evident to those skilled in the art from a reading of the present disclosure with the appended claims, and are covered within the scope of these claims.

DETAILED DESCRIPTION OF THE INVENTION

The present invention is directed to a process and composition that allows consumers and oral care professionals to determine if an oral care composition contains an effective amount of soluble fluoride ion. The composition is used in combination with oral care compositions and a color change occurs within less than 10 minutes indicating whether soluble fluoride ion is available in the oral care composition.

Another aspect of the present invention includes a signal solution for indicating the presence of soluble fluoride ions in oral care compositions that comprises a color indicator, a metal ion complex, and optionally a buffer.

Another aspect of the present invention is a process wherein a substrate is impregnated with or coated with the signal solution. The substrate can then brought into contact with an oral care composition in order to test for the presence of soluble fluoride ions.

All percentages and ratios used herein are by weight of the signal solution or test composition, unless otherwise specified. All measurements referred to herein are made at 25° C., unless otherwise specified.

While the specification concludes with claims particularly pointing out and distinctly claiming the invention, it is believed that the present invention will be better understood from the following description of preferred embodiments. All publications, patent applications, and issued patents mentioned herein are hereby incorporated in their entirety by reference. Citation of any reference is not an admission regarding any determination as to its availability as prior art to the claimed invention.

The term "effective amount" means an amount of a compound or composition sufficient to significantly induce a positive benefit, preferably the oral health benefit of preventing caries, but low enough to avoid serious side effects, i.e. to provide a reasonable benefit to risk ratio, within the sound judgment of a skilled artisan. Herein, an effective amount of soluble fluoride ions is from about 10 ppm to about 4000 ppm, preferably from about 25 ppm to 3500 ppm of soluble fluoride ion.

The term "oral care composition" as used herein means the total composition that is delivered to the oral surfaces. The oral care composition is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care compositions of the present invention are of course intended for human use, but they can equally advantageously be used for animals, such as household pets.

The term "metal" as used herein means any inorganic metal or organic metal compounds where the metal ion can interact with a color indicator or soluble fluoride ion and cause a color change.

The term "soluble" as used herein means a solution of an ionic solute that becomes saturated at a level that is greater than about 0.10 M. By contrast, if a solution of an ionic solute becomes saturated at a level that is less than about 0.01M, the solute is said to be insoluble.

Signal Solution

The signal solution of the present invention comprises a mixture of a color indicator, a metal ion source, and optionally a buffer. The signal solution can be used as a solution or it may be coated or impregnated onto a substrate. The signal solution is brought into contact with an oral care composition. If the oral care composition contains an effective amount of soluble fluoride ion, then a color change occurs within about 10 minutes.

Color Indicator

A color indicator is a natural or synthetic substance that changes color in response to the nature of its chemical environment, generally by some change in the structure or change in the electron charge. A desired color indicator for the present invention is one that has some change in structure or charge that results in a color change of the color indicator preferably in a range of pH of about 1.0 to about 7.0, more preferably between 3.0 and 6.0. Preferred color indicators for the present invention include aluminon, aluminon-alizarin, alizarin red, methyl blue, xylenol orange, fluor reagent (ALC), and mixtures thereof. Most preferred is the use of aluminon as the color indicator of the present invention.

Table 1 describes three different color indicators, that when combined with metal ions (described below) may indicate the presence of soluble fluoride ions in oral care compositions. The postulated reaction mechanism for the color change of the individual color indicators is described in Table 1. It will be understood that the mechanism for how the color indicator achieves the desired color change is not intended to be limiting of the present invention. The concentration of the color indicator in solution is preferably from 0.01% to 10% (wt % of solution); more preferably from about 0.01% to 5% (wt % of solution); and most preferably from about 0.01%-1% (wt % of solution).

TABLE 1

|  | Zirconium-Alizarin | Lanthanum-Alizarin | Al-Aluminon |
|---|---|---|---|
| Reaction Mechanism | Fluoride ions replace Alizarin to combine with Zirconium ions releasing the yellow Alizarin | Fluoride ions combine with La-Alizarin to form a complex which is blue | Fluoride ions combine with Al-Aluminon to form a complex which is colorless |
| pH | 1.0 | 4.1 | 5.0 |
| Color Change | from pink to yellow | from pink to blue | from pink to colorless |
| Other Reagents | acid | organic solvent, buffer | none |

Metal Ion

A metal ion source is a soluble metal salt that can combine with a color indicator, described above to give a color change. A desired metal ion for use herein includes salts of transition metals, representative metals, and metalloids. Preferred metal ions include aluminum ions, lanthanum ions, zirconium ions, thorium ions and mixtures thereof.

The metal ion is used to form a solution having a concentration between about 0.01 mg/mL to 1 mg/mL, preferably between about 0.05 mg/mL to 0.5 mg/mL, and most preferably about 0.05-0.15 mg/mL (calculated by mass of metal ions).

Buffer

A buffer can be used to maintain the pH of the test composition of the present invention and can also be used to control the reaction speed of the present invention. The buffer may comprise solid organic acids, solid phenols, inorganic solid acids, inorganic solid acidic salts, or mixtures thereof. Preferably the buffer comprises ammonium chloride, ammonium phosphate, ammonium sulfate, acetate, solid inorganic acids such as boric acid, and mixtures thereof. The concentration of the buffer agents may be between about 0.01% and about 30% (w/w % solution).

Soluble Fluoride Ion

Soluble fluoride ion sources are well known for use in oral care compositions as anti-caries agents. Soluble fluoride ions are contained in a number of oral care compositions for this purpose, particularly toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27, 1976 to Roberts et al; and U.S. Pat. No. 4,040,858, Aug. 9,1977 to Wason.

Application of soluble fluoride ions to dental enamel serves to protect teeth against decay. A wide variety of fluoride ion-yielding materials can be employed as sources of soluble fluoride in the instant compositions. Examples of suitable soluble fluoride ion-yielding materials are found in Briner et al; U.S. Pat. No. 3,535,421; issued Oct. 20, 1970 and Widder et al; U.S. Pat. No. 3,678,154; issued Jul. 18, 1972. Preferred soluble fluoride ion sources include sodium fluoride, potassium fluoride and ammonium fluoride. An effective amount of soluble fluoride ion for detection by the signal solution is between about 10 ppm to about 4000 ppm.

EXAMPLES AND METHOD OF PREPARATION

Examples of the invention are set forth hereinafter by way of illustration and are not intended to be in any way limiting of the invention. The following examples further describe and demonstrate embodiments within the scope of the present invention. These examples are given solely for the purpose of illustration and are not to be construed as limitations of the present invention as many variations thereof are possible without departing from the spirit and scope.

Example 1

To prepare the signal solution, 1.0 g of aluminon is dissolved in 1–3 mL of 10 wt % of NaOH. The solution is diluted to 1000 mL by adding deionized water. The pH of the solution is adjusted to 5.0 with 1 N HCl so that a 0.1 wt % Aluminon solution results. Next, 1.0 g of aluminum ion is dissolved in 1–3 mL of 10 wt % NaOH. The solution is diluted to 1000 mL by adding deionized water. The pH of the solution is adjusted to 5.0 so that the aluminum ion is present in an amount of 0.1 mg/mL. An acetate buffer is made by dissolving 200 g of sodium acetate into 900 mL deionized water. The pH of the acetate buffer solution is adjusted to 5.0.

The aluminon, aluminum ion, and acetate buffer solutions are mixed in a volume proportion of 1:5:5 so that a deep red color results. Ammonium chloride having 10–20 g/100 mL is added to the red aluminon-aluminum solution.

A strip of chromatography paper or filter paper is submerged in the aluminon-aluminum solution at room temperature for 12 hours with agitation. The paper is then dried for 5–10 hours at 80–105° C. Alternatively, the chromatography paper or filter paper can be sprayed with a spraying gun, for example Rich8, RS-506N, available in Japan, to coat one side of the paper with aluminon-aluminum solution.

The strip is used by wetting the strip with water and then coating the strip with 1–2 cm$^3$ of toothpaste. In approximately 5–8 minutes, when the strip changes color from red to colorless, there is an effective amount of soluble fluoride ion in the toothpaste.

Example 2

TABLE 2

The effect of present invention on toothpaste with different abrasive types

|  | Sample 1 | Sample 2 | Sample 3 |
|---|---|---|---|
| Fluoride type | NaF | NaF | NaF |
| Abrasive | silica | calcium hydrophosphate | aluminum hydroxide |
| Result (color change) | Pink to colorless | no change | no change |
| Time for color change | 10 minutes | NA | NA |

Table 2 shows the results of the present invention with oral care composition samples comprising differing abrasive materials. The abrasive material often contains various free ions that may react with the soluble fluoride ions in the oral care composition to form insoluble salts such as calcium fluoride ($CaF_2$). This kind of fluoride is not soluble and therefore ineffective against preventing caries. Therefore, if the free ions react with the soluble fluoride ion, then soluble fluoride ion is not available to be delivered to the tooth enamel surface. The benefits of soluble fluoride ion are therefore never delivered. However, the average consumer has no way of knowing whether the fluoride ions in his or her oral care composition are delivering an effective amount of soluble fluoride ion. Through the use of the present invention a color change allows the user to see within about 10 minutes whether the oral care composition contains soluble fluoride ions that provide an effective amount of fluoride ion to the user.

Example 3

TABLE 3

Various Concentration Of Fluoride Ion

|  | 30 ppm | 50 ppm | 100 ppm | 500 ppm |
|---|---|---|---|---|
| Color change (Yes or No) | Yes | Yes | Yes | Yes |
| Time for color change | 3 minutes | 2 minutes | 2 minutes | 1 minutes |

Therein, an effective amount of soluble fluoride ions is from about 10 ppm to about 4000 ppm. The present invention will respond within varying time periods depending on the concentration of the soluble fluoride ions in the oral care composition. As demonstrated in Table 3, above, the higher the concentration of the soluble fluoride ion in the oral care composition, the faster the color change occurs. As can be seen above, the time difference between the 50 ppm sample and 500 ppm sample is decreased by 1 minute as the concentration of soluble fluoride ion is increased by a factor of 10.

Example 4

TABLE 4

Effect Of The Present Invention On Toothpaste With Different Fluoride Type

|  | Sample 1 | Sample 4 |
|---|---|---|
| Fluoride type | NaF | NaF + MFP |
| Abrasive | silica | silica |
| Result (color change) | Pink to colorless | Pink to colorless |
| Time for color change | 10 minutes | 10 hours |

Table 4 shows the present invention using the aluminum ion/aluminon complex with oral care composition samples with different fluoride ion sources. Some oral care compositions provide soluble fluoride ions, but the concentration of the soluble fluoride ions is such that there is not an effective amount of soluble fluoride ions. The present invention allows consumers to distinguish between oral care compositions that contain effective amounts of soluble fluoride ions and those that do not.

Example 5

TABLE 5

Selectivity Of Al-Aluminon Complex With Other Ingredients In Toothpaste

|  | $F^-$ | $PO_4^{3-}$ | $Cl^-$ | $CO_3^{2-}$ |
|---|---|---|---|---|
| Concentration | 500 ppm | $1.4 \times 10^4$ ppm | $1 \times 10^4$ ppm | $1 \times 10^4$ ppm |
| color change | Yes | No | No | No |

The selective indication of soluble fluoride ions in the present invention is important in emulsions such as toothpastes since several types of ions are generally present. Acceptable soluble fluoride ion concentrations are generally about 25 to 30 times less than the concentrations of all other anions present in an oral care composition. Table 5 illustrates various anions that may be present in a toothpaste sample and the interaction of combining these anions with the present invention, here comprising an aluminon-aluminum ion complex. The anions are formed individually in a solution that is tested with the present invention. The concentrations of the representative anions present are approximately 28 times larger than the concentration of the soluble fluoride ion present. As demonstrated in Table 5, above, the anions show do not cause a color change in the present invention thereby increasing the accuracy of the present invention in measuring an effective amount of soluble fluoride ions.

What is claimed is:

1. A process for indicating the presence of soluble fluoride ions in an oral care composition which comprises:
   a. making a signal solution comprised of a color indicator and metal ion; and
   b. bringing the signal solution into contact with the oral care composition;
wherein a color change occurs if from about 10 ppm to about 4000 ppm of soluble fluoride ion is present in the oral care composition, wherein the oral care composition in the ordinary course of usage is not intentionally swallowed.

2. The process according to claim 1, wherein the signal solution comprises from about 0.01% to about 1% (w/v %) color indicator effective in a pH range of about 1.0 to 7.0.

3. The process according to claim 2, wherein the color indicator is selected from the group consisting of aluminon, aluminon-alizarine, alizarine red, methyl blue, xylenol orange, fluor reagent (ALC), and mixtures thereof.

4. The process according to claim 1, wherein the signal solution comprises from about 0.05% to about 0.5% (w/v %) metal ions selected from the group consisting of transition metals, representative metals, and metalloids, and mixtures thereof.

5. The process according to claim 4, wherein the metal ion is selected from the group consisting of aluminum, lanthanum, zirconium, and mixtures thereof.

6. The process according to claim 1, wherein the signal solution further comprises from about 0.01% to about 30% of a buffer selected from the group consisting of solid organic acids, solid phenols, inorganic solid acids, inorganic solid acidic salts and mixtures thereof.

7. The process according to claim 6, wherein the buffer is selected from the group consisting of ammonium chloride, ammonium phosphate, ammonium sulfate, acetate, and mixtures thereof.

8. The process according to claim 1, wherein the color change occurs within about 0.1 to about 10 minutes after bringing the signal solution into contact with the oral care composition.

9. The process according to claim 4, wherein the signal solution is coated onto a substrate.

10. A test composition for indicating the presence of soluble fluoride ions in oral care compositions comprising:
    a. from about 0.01% to about 1% (w/v %) aluminon;
    b. from about 0.05% to about 0.5% (w/v %) aluminum ion; and
    c. from about 0.01% to about 30% buffer;
wherein the aluminon and aluminum ion form a red complex, which in the presence of from about 10 ppm to about 4000 ppm of soluble fluoride ion in an oral care composition, results in a the red complex becoming colorless, wherein the oral care composition in the ordinary course of usage is not intentionally swallowed.

* * * * *